United States Patent [19]

Tada et al.

[11] Patent Number: 5,004,855

[45] Date of Patent: Apr. 2, 1991

[54] PROCESS FOR CONVERSION OF ETHYLBENZENE IN $C_8$ AROMATIC HYDROCARBON MIXTURE

[75] Inventors: Kuniyuki Tada, Kamakura; Eiichi Minomiya; Masatoshi Watanabe, both of Nagoya, all of Japan

[73] Assignee: Toray Industries, Inc., Tokyo, Japan

[21] Appl. No.: 234,393

[22] Filed: Aug. 19, 1988

[30] Foreign Application Priority Data

Aug. 25, 1987 [JP] Japan .................... 62-212157
Aug. 25, 1987 [JP] Japan .................... 62-212158

[51] Int. Cl.[5] .................... C07C 4/12
[52] U.S. Cl. .................... 585/489
[58] Field of Search .................... 585/489

[56] References Cited

U.S. PATENT DOCUMENTS

| | | | |
|---|---|---|---|
| 4,162,214 | 7/1979 | Maslyansky et al. | 585/489 X |
| 4,236,996 | 12/1980 | Tabak et al. | 585/489 X |
| 4,320,242 | 3/1982 | Onodera et al. | 585/489 |
| 4,399,051 | 8/1983 | Rabinovich et al. | 585/489 X |
| 4,409,413 | 10/1983 | Iwayama et al. | 585/489 X |
| 4,467,129 | 8/1984 | Iwayama et al. | 585/489 X |
| 4,482,773 | 11/1984 | Chu et al. | 585/481 |
| 4,496,784 | 1/1985 | Moorehead | 585/489 X |
| 4,511,547 | 4/1985 | Iwayama et al. | 502/77 X |

FOREIGN PATENT DOCUMENTS

| | | |
|---|---|---|
| 0109962 | 6/1984 | European Pat. Off. . |
| 0234684 | 9/1987 | European Pat. Off. . |
| 62-228031 | 10/1987 | Japan . |

*Primary Examiner*—Patrick P. Garvin
*Assistant Examiner*—George R. Fourson
*Attorney, Agent, or Firm*—Austin R. Miller

[57] ABSTRACT

Ethylbenzene can be substantially hydrode-ethylated to benzene with a minimized loss of xylene by placing a $C_8$ aromatic hydrocarbon mixture containing ethylbenzene and xylene in the presence of hydrogen in contact with a catalyst comprising 0.6 to 20.0 parts by weight of rhenium, 100 parts by weight of an acid type of a zeolite having a main cavity inlet composed of a 10-membered oxygen ring and 100 to 900 parts by weight of alumina, which has been subjected to sulfiding.

6 Claims, 1 Drawing Sheet

$C_8$
1
2
3
4
$C_{7-}$
5
6
8
9
$C_{9+}$
10
11
12
13
14
15
$C_{7-}$

PROCESS FOR CONVERSION OF ETHYLBENZENE IN $C_8$ AROMATIC HYDROCARBON MIXTURE

BACKGROUND OF THE INVENTION (1) Field of the Invention

The present invention relates to a process for the conversion of ethylbenzene in a $C_8$ aromatic hydrocarbon mixture. More particularly, the present invention relates to a process for the hydrode-ethylation of ethylbenzene to benzene.

(2) Description of the Related Art

From the industrial viewpoint, p-xylene is now the most important of xylene isomers. p-Xylene is generally prepared from a $C_8$ aromatic hydrocarbon mixture obtained by subjecting naphtha to reforming and aromatic extraction and fractional distillation or from a $C_8$ aromatic hydrocarbon mixture obtained by subjecting cracked gasoline obtained as a by-product from a thermal cracking of naphtha to aromatic extraction and fractional distillation. Although the composition of this starting $C_8$ aromatic hydrocarbon mixture varies over a wide range, the mixture generally comprises 10 to 40% by weight of ethylbenzene, 12 to 25% by weight of p-xylene, 30 to 50% by weight of m-xylene and 12 to 25% by weight of o-xylene. The physical properties of the respective components of the $C_8$ aromatic hydrocarbon mixture are as follows.

| | Melting Point (°C.) | Boiling Point (°C.) |
|---|---|---|
| Ethylbenzene | −94.4 | 136.2 |
| p-Xylene | 13.4 | 138.4 |
| m-Xylene | −47.4 | 139 |
| o-Xylene | −28.0 | 142 |

In the industrial process for the preparation of p-xylene, in general, the starting $C_8$ aromatic hydrocarbon mixture is first fed to the p-xylene-separating step, where p-xylene is separated and recovered. As pointed out hereinbefore, the boiling point of p-xylene is very close to the boiling point of m-xylene, and therefore, separation by distillation is industrially disadvantageous. Accordingly, separation is accomplished by a deep freeze separation process utilizing the difference of the melting point or the adsorptive separation process in which p-xylene is selectively adsorbed in a porous solid adsorbent. The remaining $C_8$ aromatic hydrocarbon mixture in which the p-xylene content has been reduced at the p-xylene-separating step is fed to the isomerizing step, where isomerization is carried out so that a p-xylene concentration corresponding substantially to the thermodynamic equilibrium composition is attained. Then, the isomerized mixture is recycled to the p-xylene-separating step together with a fresh starting $C_8$ aromatic hydrocarbon mixture. The circulation system comprising the above-mentioned p-xylene-separating step and xylene-isomerizing step is called "separation-isomerization cycle" hereinafter. Note, if circumstances require same, o-xylene is separated and recovered by distillation.

As pointed out hereinbefore, a considerable amount of ethylbenzene is contained in the $C_8$ aromatic hydrocarbon mixture. Accordingly, to prevent an accumulation of ethylbenzene in the separation-isomerization cycle, ethylbenzene is removed and ethylbenzene in an amount determined by the removal ratio is circulated in the separation-isomerization cycle.

As the amount of ethylbenzene circulated in the separation-isomerization cycle is small, the amount of circulated liquid is reduced and the energy consumption required at each of the p-xylene-separating step and xylene-isomerizing step is reduced, and thus a great economical advantage is obtained. Nevertheless, according to the conventional technique, it is difficult to reduce the amount of ethylbenzene circulated in the separation-isomerization cycle by an inexpensive method, to an extent such that the ethylbenzene content can be regarded as substantially zero.

According to the method customarily adopted for removing ethylbenzene, an isomerizing catalyst having an ethylbenzene-converting activity is used at the isomerizing step whereby ethylbenzene is converted to xylene or a substance that can be easily separated from xylene at the isomerization reaction. For example, there can be mentioned (1) a method in which ethylbenzene is converted to xylene by a dual-functional catalyst comprising a platinum and a solid acid (U.S. Pat. No. 3,409,699), (2) a method in which ethylbenzene is converted to benzene and diethylbenzene by transalkylation reaction (U.S. Pat. Nos. 3,856,871 and 4,120,908), and (3) a method in which ethylbenzene is converted to benzene by de-ethylation reaction (European Patent No. 138,617). According to methods (1) and (2), in view of the reaction principle, it is difficult to increase the conversion of ethylbenzene. According to method (3), in view of the reaction principle, it is possible to increase the conversion of ethylbenzene, but even if the conversion of ethylbenzene can be practically increased, if the conventional flow for converting and removing ethylbenzene in the separation-isomerization cycle is used, since ethylbenzene is contained in a relatively large amount in the starting $C_8$ aromatic hydrocarbon mixture, reduction of the ethylbenzene concentration at the p-xylene-separating step is limited, and it is difficult to drastically reduce the ethylbenzene concentration in the liquid circulated in the separation-isomerization cycle.

As one feasible selection, U.S. Pat. No. 4,159,282 discloses a method in which the majority of ethylbenzene contained in the starting $C_8$ aromatic hydrocarbon mixture is converted by using a zeolite as a catalyst in an independent reaction vessel before the starting $C_8$ aromatic hydrocarbon mixture is fed to the separation-isomerization cycle, but no specific example is shown therein. The invention disclosed in this U.S. patent is characterized in that a crystalline aluminosilicate zeolite having a crystal size of at least 1 micron and a silica/alumina ratio of at least 12 not only isomerizes xylene but also selectively converts ethylbenzene. However, in all of the specific examples, the highest conversion of ethylbenzene is only 43.5%.

Namely, according to the conventional techniques, in view of the reaction principle, it is impossible to increase the conversion of ethylbenzene, or even where there is no upper limit to the conversion of ethylbenzene in view of the reaction principle, an increase of the conversion of ethylbenzene tends to result in an increase of the loss of xylene, and as the conversion of ethylbenzene approaches 100%, the loss of xylene is drastically increased, with the result that the increase of the conversion of ethylbenzene with a small loss of xylene cannot be attained.

SUMMARY OF THE INVENTION

It is a primary object of the present invention to provide a process for converting ethylbenzene in a $C_8$ aromatic hydrocarbon mixture containing ethylbenzene and xylene to benzene.

Another object of the present invention is to provide a process for converting ethylbenzene, in which the conversion of ethylbenzene can be increased with a reduced loss of xylene.

Still another object of the present invention is to provide a high-performance catalyst for the hydrodeethylation of ethylbenzene, which has a high activity for converting ethylbenzene in a $C_8$ aromatic hydrocarbon mixture containing ethylbenzene and xylene to benzene and having a much reduced loss of xylene by a side reaction.

Still another object of the present invention is to provide a process in which the ethylbenzene concentration in a liquid circulated in the separation-isomerization cycle can be reduced at a low cost on an industrial scale.

A still further object of the present invention is to provide a process in which the energy consumption required at the separation-isomerization cycle can be reduced while reducing the ethylbenzene concentration in a liquid circulated in the separation-isomerization cycle to substantially zero.

In accordance with the present invention, there is provided a process for the conversion of ethylbenzene in a $C_8$ aromatic hydrocarbon mixture, which comprises placing a $C_8$ aromatic hydrocarbon mixture containing ethylbenzene and xylene in the presence of hydrogen in contact with a catalyst comprising 0.6 to 20.0 parts by weight of rhenium, 100 parts by weight of an acid type of a zeolite having a main cavity inlet composed of a 10-membered oxygen ring and 100 to 900 parts by weight of alumina, said catalyst having been subjected to a sulfiding treatment, to effect hydrode-ethylation of ethylbenzene to benzene.

Other and further objects, features and advantages of the present invention will become more fully apparent from the following description.

BRIEF DESCRIPTION OF THE DRAWING

The drawing illustrates one embodiment of the process of the preparation of xylene according to the present invention.

DESCRIPTION OF THE PREFERRED EMBODIMENTS

Figure 1:
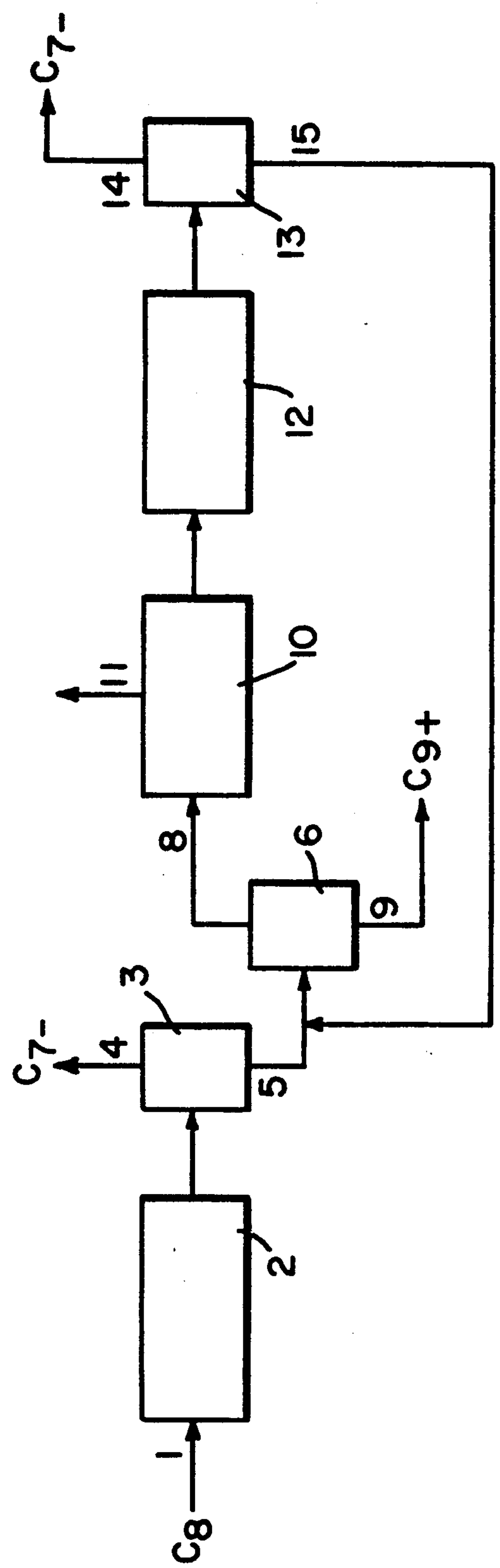

Any $C_8$ aromatic hydrocarbon mixture containing ethylbenzene and xylene can be used as the starting material in the present invention, without limitation, but starting materials for the production of p-xylene, such as a $C_8$ aromatic hydrocarbon mixture obtained by reforming naphtha and aromatic extraction and fractional distillation and a $C_8$ aromatic hydrocarbon mixture obtained by subjecting cracked gasoline obtained as a by-product from thermal cracking of naphtha to aromatic extraction and fractionation, are preferably used. The $C_8$ aromatic hydrocarbon mixture may contain small amounts of $C_7$ and $C_9$ aromatic hydrocarbons and/or $C_7$ through $C_9$ non-aromatic hydrocarbons in addition to $C_8$ aromatic hydrocarbons. The total content of these compounds other than $C_8$ aromatic hydrocarbons is ordinarily lower than 10% by weight based on the $C_8$ aromatic hydrocarbons.

In the present invention, a catalyst comprising rhenium, an acid type of a zeolite having a main cavity inlet composed of a 10-membered oxygen ring and alumina, which has been subjected to a sulfurization treatment, is used.

The catalyst used in the present invention comprises a zeolite having a main cavity inlet composed of a 10-membered oxygen ring. As is well-known, the zeolite has, as the substrate, a skeleton comprising $SiO_4$ tetrahedrons and $AlO_4$ tetrahedrons arranged at an $O/(Si+Al)$ atomic ratio of 2 (inclusive of a skeleton in which Si or Al is isomorphically substituted with other metal), and a negative charge structurally generated by this skeleton is neutralized by a cation such as a metal ion. Present in this skeleton are cavities (pores) having a molecular size, which communicate with the outside, and the shape and size of the cavities vary depending upon the particular crystalline aluminosilicate zeolite. In a zeolite having a main cavity inlet composed of an 8-membered oxygen ring, the diffusion of ethylbenzene in the main cavity where a catalytic active site is present is restricted, and in a catalyst having a main cavity inlet composed of a 12-membered oxygen ring, ethylbenzene easily diffuses in the main cavity, but transalkylation as a side reaction becomes vigorous and the loss of xylene increases. Accordingly, these zeolites are not preferred. As the catalyst having a main cavity inlet composed of a 10-membered oxygen ring substantially free of zeolites having pores defined by 8- or 12-membered oxygen rings, which is used in the present invention for the reasons just discussed above, there can be mentioned clinoptilolite, ferrierite, ZSM-5, ZSM-11, Zeta 3 disclosed in German Laid-Open Specification No. 2,548,695, and a pentasil type zeolite disclosed in U.S. Pat. No. 4,511,547. The ZSM-5 and the pentasil type zeolite disclosed in U.S. Pat. No. 4,511,547 are especially preferred. Preferably, $SiO_2/Al_2O_3$ molar ratio of the zeolite is at least 15, especially at least 35.

In the present invention, an acid type zeolite is used. As is well-known, the acid type zeolite contains a proton or a divalent or polyvalent cation such as a rare earth element ion as at least a part of the ion-exchangeable cation. In general, the acid type can be obtained by exchanging at least a part of an alkali metal ion of a zeolite having a monovalent alkali metal ion such as sodium with a proton or a divalent or polyvalent cation, or by exchanging at least a part of an alkali metal ion with an ammonium cation which can be converted to a proton by calcination and calcining the zeolite.

In the catalyst used in the present invention, alumina is combined with the acid type of the zeolite having a main cavity inlet composed of a 10-membered oxygen ring. Any alumina customarily used as the starting material of catalysts, such as x-alumina, $\eta$-alumina, $\gamma$-alumina and $\theta$-alumina, can be used as the alumina in the present invention. Of course, alumina hydrates that can be converted to alumina by a heat treatment, such as gibbsite, bialite and boehmite, can be used as the alumina material. The alumina is used in an amount of 100 to 900 parts by weight per 100 parts by weight of the zeolite. If the amount of alumina is smaller than 100 parts by weight, an undesirable side reaction becomes serious and if the amount of alumina is larger than 900 parts by weight, the catalytic activity per unit weight of the catalyst is reduced. Alumina may be contained as the binder of the catalyst.

The catalyst used in the present invention further comprises rhenium. Rhenium is indispensable for shifting the equilibrium by hydrogenating ethylene, formed by a de-ethylation of ethylbenzene, to ethane, and thereby increasing the conversion of ethylbenzene. As the catalyst component having an analogous function, there can be mentioned metal elements of the group VIB, such as molybdenum, and metal elements of the group VIII, such as nickel and platinum, but these metal elements do not have a sufficient capacity for hydrogenating ethylene or in that these metal elements simultaneously cause hydrogenation of the aromatic ring. In the catalyst used in the present invention, rhenium is used in an amount of 0.6 to 20.0 parts as the rhenium atom per 100 parts by weight of the zeolite. If the amount of rhenium is smaller than 0.6 part by weight, the activity of the catalyst for hydrode-ethylating ethylbenzene is reduced and the loss of xylene by a side reaction relatively increased. If the amount of rhenium is larger than 20.0 parts by weight, a side reaction by rhenium, such as hydrocracking, becomes serious.

In the present invention, preferably the respective components of rhenium, zeolite and alumina are uniformly dispersed in the catalyst. In general, powders of the zeolite and alumina are intimately mixed together and molded into a catalyst. Known molding methods such as extrusion molding, compression molding, and rolling molding can be adopted for the molding. If necessary, a binder such as alumina sol or clay can be added at the molding step. The amount of the binder is up to 30% by weight, preferably up to 20% by weight, based on the sum of the zeolite and alumina. If alumina is used as the binder, the amount of alumina inclusive of alumina intended to be used as the binder must be adjusted to 100 to 900 parts by weight per 100 parts by weight of the zeolite.

Rhenium can be supported on the catalyst by a known method such as an impregnation method, an ion exchange method, or a mixing method. In view of the dispersibility of rhenium and operation ease, the impregnation method is preferable. The impregnation is accomplished by placing a molded body of the zeolite and alumina in contact with an aqueous solution of a water-soluble rhenium compound such as perrhenic acid or ammonium perrhenate or converting the rehenium compound to rhenium at the molding step.

The catalyst used in the present invention is subjected to a sulfiding treatment before being applied to the hydrode-ethylation of ethylbenzene. By this sulfiding treatment, rhenium is changed to a sulfide. Any method capable of converting rhenium to a sulfide can be adopted for the sulfiding treatment. In general, after rhenium has been supported, the sulfurization treatment is carried out in a current of hydrogen sulfide at room temperature to 500° C., preferably 100° to 450° C. The time of the sulfiding treatment is not particularly critical, so long as the treatment is conducted after the rhenium has been supported. For example, the sulfiding treatment can be carried out in a reaction vessel just before the hydrode-ethylation of ethylbenzene or before the calcination for activation in air. Note, in this sulfiding treatment, the ethylbenzene-converting activity of the catalyst is increased and the loss of xylene due to the side reaction is decreased.

In the present invention, the reaction is carried out in the presence of hydrogen. Hydrogen is used in an amount of 0.2 to 20 moles, preferably 1 to 10 moles, per mole of the $C_8$ aromatic hydrocarbon mixture.

The reaction of hydrode-ethylation of ethylbenzene according to the present invention is carried out under conditions similar to those ordinarily adopted for the gas-phase conversion reaction of a $C_8$ aromatic hydrocarbon. More specifically, the reaction is carried out at a temperature of 300° to 530° C., preferably 350° to 480° C., a pressure of 0.5 to 25 kg/cm$^2$, preferably 3 to 20 kg/cm$^2$, and a weight space velocity of 0.2 to 30 hr$^{-1}$, preferably 2 to 20 hr$^{-1}$.

According to the process of the present invention, ethylbenzene in a $C_8$ aromatic hydrocarbon mixture can be converted to benzene at a conversion of at least 90%. Moreover, by appropriately selecting the reaction conditions, the conversion can be elevated to 95% or higher, and ethylbenzene can be substantially removed from the $C_8$ aromatic hydrocarbon mixture.

An embodiment of the process for the preparation of p-xylene according to the present invention will now be described with reference to the accompanying drawings. A starting $C_8$ aromatic hydrocarbon mixture is fed through a line 1 together with hydrogen to an ethylbenzene-de-ethylating reactor 2 loaded with a hydrode-ethylation catalyst, and the majority of ethylbenzene is hydrode-ethylated to benzene. The reaction product is substantially free of ethylbenzene and is fed to a distillation column 3, where hydrocarbons having up to 7 carbon atoms are separated through a line 4. The hydrode-ethylation product comprising aromatic hydrocarbons having at least 8 carbon atoms is fed to a distillation column 6 through a line 5 together with a xylene isomerization product comprising aromatic hydrocarbons having at least 8 carbon atoms, and aromatic hydrocarbons having at least 9 carbon atoms are separated through a line 9. Then, the residual $C_8$ aromatic hydrocarbon mixture is fed to a p-xylene separator 10 through a line 8. In the present invention, any method adopted for the usual industrial p-xylene production process, such as the crystallization method and the absorptive separation method, can be adopted for the p-xylene-separation. The process of the present invention is especially effective for the adsorptive separation method, in which the separation of p-xylene from ethylbenzene is difficult. p-Xylene is recovered through a line 11 and the $C_8$ aromatic hydrocarbon mixture having a reduced p-xylene content is isomerized in a xylene-isomerizing reactor 12 so that a p-xylene concentration close to the thermodynamic equilibrium composition is obtained. Any method used in the ordinary p-xylene production process can be adopted for the isomerization of xylene. In the process of the present invention, the ethylbenzene concentration in the liquid circulated in the separation-isomerization cycle is controlled to a very low level and a substantial conversion of ethylbenzene is not necessary at the xylene-isomerizing step. Therefore, the process of the present invention is especially preferably applied to a process in which an increase of the conversion of ethylbenzene is difficult in view of the principle, for example, the liquid phase isomerization reaction process. The liquid isomerization reaction product which has been isomerized at the xylene-isomerizing reactor 12 to a p-xylene concentration close to the thermodynamic equilibrium composition is fed to a distillation column 13, hydrocarbons having up to 7 carbon atoms are separated through a line 14, and aromatic hydrocarbons having at least 8 carbon atoms, contained in the liquid isomerization reaction product, are recycled to the distillation column 6 through a line 15.

As is apparent from the foregoing embodiment, the process of the present invention can be carried out easily in combination with the ordinary process for the production of p-xylene.

The present invention will be now described in detail with reference to the following examples.

EXAMPLE 1

According to the teaching of U.S. Pat. No. 4,511,547, a powdery pentasil type zeolite having an $SiO_2/Al_2O_3$ molar ratio of 46.4 was synthesized from an aqueous mixture comprising hydrous silicic acid, sodium aluminate, sodium hydroxide, tartaric acid and water. Then, 100 parts by weight of this pentasil type zeolite powder was kneaded together with 40 parts by weight of powdery γ-alumina and 75 parts by weight, as $Al_2O_3$, of alumina sol as the binder and the kneaded mixture was extrusion-molded to a size of 14 to 24 mesh and calcined in air at 500° C. for 2 hours. The molded body was subjected to a one-time ion exchange using an aqueous solution containing ammonium chloride in an amount of 11 parts by weight per 100 parts by weight of the zeolite (solid-liquid ratio of 2.0 l/g, about 90° C.), washed thoroughly with water, dried at 120° C. for 15 hours and immersed in an aqueous solution containing rhenium oxide (VII) in an amount of 2.5 parts as the rhenium atom per 100 parts by weight of the zeolite (solid-liquid ratio of 1.2 l/kg, room temperature, 4 hours). After draining, the impregnated molded body was dried at 120° C. for 15 hours, subjected to sulfiding in a hydrogen sulfide current at 250° C. for 2 hours, and calcined in air at 500° C. for 2 hours to obtain a catalyst A. This catalyst A contained 2.5 parts by weight of rhenium and 475 parts by weight of alumina per 100 parts by weight of the zeolite.

A starting $C_8$ aromatic hydrocarbon mixture obtained by reforming naphtha in a fixed bed circulation reaction apparatus and performing aromatic extraction and fractional distillation was subjected to hydrode-ethylation by using the catalyst A. The reaction conditions and results are shown in Table 1. The starting $C_8$ aromatic hydrocarbon mixture used for hydrode-ethylation had the following composition.

| | |
|---|---|
| $C_8$ naphthene paraffin | 0.03% by weight |
| $C_9$ naphthene paraffin | 0.06% by weight |
| toluene | 1.00% by weight |
| ethylbenzene | 16.65% by weight |
| xylene | 82.26% by weight |

EXAMPLE 2

A mixture formed by kneading 100 parts by weight of a powdery pentasil type zeolite having an $SiO_2/Al_2O_3$ molar ratio of 46.4, prepared in the same manner as described in Example 1, with 300 parts by weight of powdery γ-alumina and 60 parts by weight, as $Al_2O_3$, of alumina sol as the binder was extrusion-molded to a size of 14 to 24 mesh and calcined in air at 500° C. for 2 hours. The molded body was subjected to a one-time ion exchange using an aqueous solution containing ammonium chloride and calcium chloride in amounts of 11 parts by weight and 5 parts by weight, respectively, per 100 parts by weight of the zeolite (solid-liquid ratio of 2.0 l/kg, about 90° C.), washed thoroughly with water, dried at 120° C. for 15 hours, and immersed in an aqueous solution containing rhenium oxide in an amount of 2.8 parts as the rhenium atom per 100 parts by weight of the zeolite (solid-liquid ratio of 1.2 l/kg, room temperature, 4 hours). After draining, the impregnated molded body was dried at 120° C. for 5 hours, subjected to sulfiding in a hydrogen sulfide current at 250° C. for 2 hours, and calcined in air at 500° C. for 2 hours to obtain a catalyst B. This catalyst contained 2.8 parts by weight of rhenium and 360 parts by weight of alumina per 100 parts by weight of the zeolite.

Using the so-obtained catalyst B, the reaction was carried out in the same manner as described in Example 1. The reaction conditions and results are shown in Table 1.

EXAMPLE 3

According to the teaching of U.S. Pat. No. 4,151,189, powdery zeolite ZSM-5 having an $SiO_2/Al_2O_3$ molar ratio of 70.0 was synthesized from an aqueous mixture comprising sodium silicate, aluminum sulfate, n-propylamine, sulfuric acid and water. Then, 100 parts by weight of the so-obtained powdery zeolite ZSM-5 was kneaded with 150 parts by weight of γ-alumina and 38 parts by weight as $Al_2O_3$ of alumina sol as the binder and the kneaded mixture was extrusion-molded to a size of 14 to 24 mesh and calcined in air at 500° C. for 2 hours. The molded body was subjected to a one-time ion exchange using an aqueous solution containing ammonium chloride in an amount of 11 parts by weight per 100 parts by weight of the zeolite (solid-liquid ratio of 2.0 l/g, about 90° C.), washed sufficiently with water, dried at 120° C. for 15 hours and immersed in an aqueous solution containing rhenium oxide (VII) in an amount of 1.8 parts by weight per 100 parts by weight of the zeolite (solid-liquid ratio of 1.2 l/kg, room temperature, 4 hours). After draining, the impregnated molded body was dried at 120° C. for 15 hours, subjected to a sulfurization treatment in a hydrogen sulfide current at 250° C. for 2 hours and calcined in air at 500° C. for 2 hours to obtain a catalyst C. The so-obtained catalyst C contained 1.8 parts by weight of rhenium and 188 parts by weight of alumina per 100 parts by weight of the zeolite.

Using the catalyst C, the reaction was carried out in the same manner as described in Example 1. The reaction conditions and results are shown in Table 1.

COMPARATIVE EXAMPLE 1

A molded body comprising a pentasil type zeolite having an $SiO_2/Al_2O_3$ molar ratio of 46.4 and γ-alumina, prepared in the same manner as described in Example 2, was subjected to a one-time ion exchange treatment using an aqueous solution containing 11 parts by weight of ammonium chloride and 5 parts by weight of calcium chloride per 100 parts by weight of the zeolite (solid-liquid ratio of 2.0 l/kg, about 90° C.), washed thoroughly with water, dried at 120° C. for 15 hours and immersed in an aqueous solution containing nickel nitrate in an amount of 4.0 parts by weight per 100 parts by weight of the zeolite (solid-liquid ratio of 1.2 l/g, room temperature, 4 hours). After draining, the impregnated molded body was dried at 120° C. for 15 hours and calcined in air at 500° C. for 2 hours to obtain a catalyst D containing nickel instead of rhenium.

Using this catalyst D, the reaction was carried out in the same manner as described in Example 1. The reaction conditions and results are shown in Table 1. As shown in Table 1, the loss of xylene was large in the case of the catalyst containing nickel.

COMPARATIVE EXAMPLE 2

A catalyst E was prepared in the same manner as described in Example 2 except that γ-alumina was not used. By using this catalyst E, the reaction was carried out in the same manner as described in Example 1. The reaction conditions and results are shown in Table 1.

COMPARATIVE EXAMPLE 3

A catalyst F was prepared in the same manner as described in Example 2 except that the sulfiding treatment was not carried out. Using this catalyst F, the reaction was carried out in the same manner as described in Example 1. The reaction conditions and results are shown in Table 1.

TABLE 1

| Catalyst | Example 1 A | Example 2 B | | Example 3 C | Comparative Example 1 D | Comparative Example 2 E | Comparative Example 3 F | Comparative Example 4 G | Comparative Example 5 H | | Comparative Example 6 I |
|---|---|---|---|---|---|---|---|---|---|---|---|
| WHSV ($hr^{-1}$) | 3.5 | 3.5 | 3.5 | 3.5 | 3.5 | 3.5 | 3.5 | 3.5 | 3.5 | 3.5 | 3.5 |
| $H_2/F$ (mole/mole) | 3 | 3 | 3 | 3 | 3 | 3 | 3 | 3 | 3 | 3 | 3 |
| Temperature (°C.) | 450 | 405 | 435 | 430 | 405 | 415 | 445 | 450 | 405 | 435 | 405 |
| Pressure ($kg/cm^2 \cdot G$) | 9 | 9 | 9 | 9 | 9 | 9 | 9 | 9 | 9 | 9 | 9 |
| EB conversion (%)* | 97.4 | 90.4 | 99.3 | 97.6 | 88.3 | 97.8 | 98.9 | 18.4 | 54.6 | 82.7 | 90.7 |
| Xy loss (wt %)** | 4.5 | 3.4 | 7.2 | 7.6 | 13.4 | 10.5 | 9.1 | 7.0 | 2.2 | 3.3 | 8.7 |

Note

*EB conversion = Conversion of ethylbenzene $$= \frac{\text{Ethylbenzene concentration in starting material} - \text{Ethylbenzene concentration in product}}{\text{Ethylbenzene concentration in starting material}} \times 100$$

**Xy loss = Loss of xylene $$= \frac{\text{Xylene concentration in starting material} - \text{Xylene concentration in product}}{\text{Xylene concentration in starting material}} \times 100$$

COMPARATIVE EXAMPLE 4

A catalyst G was prepared in the same manner as described in Example 2 except that synthetic mordenite having an $SiO_2/Al_2O_3$ molar ratio of 10 having a main cavity inlet composed of a 12-membered oxygen ring was used instead of the pentasil type zeolite.

Using this catalyst G, the reaction was carried out in the same manner as described in Example 1. The reaction conditions and results are shown in Table 1. The activity of converting ethylbenzene was low and the loss of xylene relative to the conversion of ethylbenzene was large.

COMPARATIVE EXAMPLE 5

A catalyst H having a high alumina content was prepared in the same manner as described in Example 2 except that the amount of powdery γ-alumina was changed to 940 parts by weight.

Using this catalyst H, the reaction was carried out in the same manner as described in Example 1. The reaction conditions and obtained results are shown in Table 1. As shown in Table 1, the activity of converting ethylbenzene was low.

COMPARATIVE EXAMPLE 6

A molded body was prepared by kneading 100 parts by weight of a powdery pentasil type zeolite having an $SiO_2/Al_2O_3$ molar ratio of 46.4, which was prepared in the same manner as described in Example 2, with 300 parts by weight of powdery γ-alumina and 60 parts by weight as $Al_2O_3$ of alumina sol as the binder, extrusion-molding the kneaded mixture to a size of 14 to 24 mesh and calcining the molded mixture in air at 500° C. for 2 hours. The molded body was subjected to a one-time ion exchange using an aqueous solution containing ammonium chloride and calcium chloride in amounts of 11 parts by weight and 5 parts by weight, respectively, per 100 parts by weight of the zeolite (solid-liquid ratio of 2.0 l/kg, about 90° C.), washed thoroughly with water, dried at 120° C. for 15 hours, and immersed in an aqueous solution containing chloroplatinic acid in an amount of 0.1% by weight as the platinum atom based on the catalyst (solid-liquid ratio of 1.2 l/g, room temperature, 4 hours). After draining, the impregnated molded body was dried at 120° C. for 15 hours and calcined in air a 550° C. for 2 hours to obtain a catalyst I containing platinum instead of rhenium. Using this catalyst I, the reaction was carried out in the same manner as described in Example 1. The reaction conditions and results are shown in Table 1.

EXAMPLE 4

According to the teaching of U.S. Pat. No. 4,511,547, a powdery pentasil type zeolite having an $SiO_2/Al_2O_3$ molar ratio of 49.5 was synthesized from an aqueous mixture comprising hydrous silicic acid, sodium aluminate, sodium hydroxide, tartaric acid, and water. Then, 100 parts by weight of this powdery pentasil type zeolite was kneaded together with 300 parts by weight of powdery γ-alumina and 60 parts by weight as $Al_2O_3$ of alumina sol as the binder, and the kneaded mixture was extrusion-molded to a size of 14 to 24 mesh and calcined in air at 500° C. for 2 hours. The molded body was subjected to a one-time ion exchange using an aqueous solution containing 1.3% by weight of ammonium chloride (solid-liquid ratio of 2.0 l/kg, about 90° C.), washed thoroughly with water, dried at 120° C. for 15 hours, and immersed in an aqueous solution containing rhenium oxide (VII) in an amount of 2.3 parts as the rhenium atom per 100 parts by weight of the zeolite (solid-liquid ratio of 1.2 l/g, room temperature, 4 hours). After draining, the impregnated molded body was dried at 120° C. for 15 hours, subjected to sulfiding in a hydrogen sulfide current at 250° C. for 2 hours, and calcined in air at 550° C. for 2 hours to obtain a catalyst J containing rhenium and the acid type pentasil zeolite. The zeolite J contained 2.3 parts by weight of rhenium and 360 parts by weight of alumina per 100 parts by weight of the zeolite.

The process for the production of p-xylene, as illustrated in the drawings, was constructed by combining the step of hydrode-ethylating ethylbenzene with the catalyst J with the step of separating p-xylene by the simulated moving bed method using a zeolite type adsorbent and the step of isomerizing xylene with a zeolite type catalyst. The conditions adopted at the respective steps were as follows.

| | |
|---|---|
| (1) Hydrode-ethylation of Ethylbenzene | |
| Catalyst | J |
| WHSV | 3.5 $hr^{-1}$ |
| $H_2/F$ | 5 mole/mole |
| Temperature | 450° C. |
| Pressure | 9 $kg/cm^2G$ |
| Starting material | 1.03% of toluene, 16.70% of ethylbenzene, 82.25% of xylene and 0.02% of $C_9$ aromatic hydrocarbons |
| (2) Separation of p-Xylene | |
| Method | liquid phase simulated moving bed method |
| Adsorbent | K-exchanged Y type zeolite |
| Desorbent | p-diethylbenzene |
| Purity of p-xylene product | 99.4% |
| (3) Isomerization of Xylene | |
| Method | fixed bed gas phase circulation reaction method |
| Catalyst | Re-mordenite type zeolite-pentasil type zeolite |
| pX/Xy* after isomerization | 23.0% |
| Conversion** of ethylbenzene | 50 to 65% |

*pX/Xy = [p-xylene/(p-xylene + m-xylene + o-xylene] × 100
**Conversion of ethylbenzene = [(ethylbenzene concentration in starting material to be isomerized - ethylbenzene concentration in isomerization reaction product-)/ethylbenzene concentration in starting material to be isomerized] × 100

The starting $C_8$ aromatic hydrocarbon mixture was passed through the step of hydrode-ethylation of ethylbenzene and then fed to the separation-isomerization cycle to prepare p-xylene. In the liquid introduced into the p-xylene separator, the ethylbenzene concentration was 0.07% by weight, and in the liquid introduced in the xylene-isomerizing reactor, the xylene concentration was 22.6% by weight and the ethylbenzene concentration was 0.08% by weight.

p-Xylene was prepared in the same manner as described above except that the step of hydrode-ethylating ethylbenzene was omitted. In the liquid introduced in the p-xylene separator, the ethylbenzene concentration was 8.2% by weight, and in the liquid introduced in the xylene-isomerizing reactor, the xylene concentration was 20.6% by weight and the ethylbenzene concentration was 10.2% by weight.

When the former process of the present invention was compared with the latter comparative process with respect to the energy consumption required at the separation-isomerization cycle, it was found that the ratio of the energy consumption required in the former process to that in the latter process was 0.8.

We claim:

1. A process for preparing p-xylene from a $C_8$ aromatic hydrocarbon mixture containing ethylbenzene and xylene, which comprises the steps of:

(a) converting ethylbenzene in said $C_8$ aromatic hydrocarbon mixture to benzene by contacting said $C_8$ aromatic hydrocarbon mixture in the presence of hydrogen with a catalyst comprising 0.6 to 20.0 parts by weight of rhenium, 100 parts by weight of a zeolite which consists essentially of an acid type zeolite having a main cavity inlet composed of a 10-membered oxygen ring and 100 to 900 parts by weight of alumina, said catalyst being substantially free of zeolites having main cavity inlets composed of 8-membered or 12-membered oxygen rings, and said catalyst having been subjected to a sulfiding treatment to effect hydrode-ethylation of ethylbenzene;

(b) separating $C_8$ aromatic hydrocarbon mixture from the resulting conversion reaction mixture; and (c) feeding the separated $C_8$ aromatic hydrocarbon mixture to a circulation system comprising a p-xylene separating step and a xylene-isomerizing step to produce p-xylene.

2. A process according to claim 1, wherein the sulfiding treatment is carried out in a hydrogen sulfide current at a temperature of 100° to 450° C.

3. A process according to claim 1, wherein the sulfiding treatment is carried out after rhenium has been supported on the catalyst.

4. A process according to claim 1, wherein the zeolite having a main cavity inlet composed of a 10-membered oxygen ring is a pentasil type zeolite.

5. A process according to claim 1, wherein the zeolite having a main cavity inlet composed of a 10-membered oxygen ring has an $SiO_2/Al_2O_3$ molar ratio of at least 35.

6. A process according to claim 1, wherein the hydrode-ethylation reaction is carried out at a temperature of 350° to 480° C., a pressure of 3 to 20 $kg/cm^2$, a hydrogen/$C_8$ aromatic hydrocarbon molar ratio of from 1 to 10 and a weight hourly space velocity of 2 to 20 $hr^{-1}$.

* * * * *